United States Patent [19]

Wyatt

[11] Patent Number: 4,810,875

[45] Date of Patent: Mar. 7, 1989

[54] METHOD AND APPARATUS FOR EXAMINING THE INTERIOR OF SEMI-OPAQUE OBJECTS

[75] Inventor: Philip J. Wyatt, Santa Barbara, Calif.

[73] Assignee: Wyatt Technology Corporation, Santa Barbara, Calif.

[21] Appl. No.: 9,447

[22] Filed: Feb. 2, 1987

[51] Int. Cl.⁴ .................. A61B 5/00; G01N 21/47
[52] U.S. Cl. .................................. 250/227; 128/633; 128/664; 128/665
[58] Field of Search .............. 250/227, 213 VT, 578; 128/303.1, 362, 633, 664, 665; 378/37; 350/96.1, 96.26; 356/448

[56] References Cited

U.S. PATENT DOCUMENTS

Re. 29,229  5/1977  Girard et al. ................... 351/160
3,174,414   3/1965  Myer ............................. 350/96.1
3,947,088   3/1976  French ........................... 356/448
4,334,736   6/1982  Herbert .......................... 350/418
4,515,165   5/1985  Carroll .......................... 128/664
4,555,179  11/1985  Langerholc et al. .
4,555,731  11/1985  Zinchuk ...................... 250/213 VT
4,600,011   7/1986  Watmough ...................... 128/664
4,649,275   3/1987  Nelson et al. .................. 128/665
4,651,744   3/1987  Bristow et al. .

FOREIGN PATENT DOCUMENTS 1513676  2/1968  France .
2126717  3/1984  United Kingdom .

OTHER PUBLICATIONS

Girolamo et al, "Clinical Diaphanography-Its Present Perspective", CRC Critical Reviews in Oncology/Hematology, vol. 2, Iss. 1, pp. 1–31, 1984.

Cohen, "Infrared Viewer and Image Intensifier", Am. J. of Opthamology, p. 432, Mar. 1979.

*RNM Images*, Brochure, Feb. 1983.

Merritt et al., "Real-time Transillumination Light Scanning of the Breast", Radiographics, vol. 4, No. 6, pp. 989–1009, Nov. 1984.

"Inspection System For Particulate and Defect Detection on Product Wafers"; IBM Tech. Disc. Bull., vol. 27, No. 12, May 1985, pp. 6971–6973.

Vogel, "Method of Characterizing the Optical Quality of Glass", Applied Optics, vol. 22, No. 15, Aug. 1983, pp. 2241–2242.

*Primary Examiner*—Edward P. Westin
*Attorney, Agent, or Firm*—Philip J. Wyatt

[57] ABSTRACT

A highly collimated light beam, such as produced by a laser, is coupled by optical means directly onto a semi-opaque object such as a human breast. The light transmitted and scattered therein is collected at a fixed surface element and direction relative to the incident light, and coupled optically into an image intensifier, preserving the spatial intensity variations passing through said fixed surface element. The intensified image is then collected on an array of detector elements which digitizes and then transfers said preserved image into memory means where it is processed to characterize the interior of said object. This invention has particular application to the early detection of breast cancer.

47 Claims, 7 Drawing Sheets

METHOD AND APPARATUS FOR EXAMINING THE INTERIOR OF SEMI-OPAQUE OBJECTS

BACKGROUND OF THE INVENTION

1. Field of the Invention

This invention concerns a new method for measuring light transmitted through a semi-opaque object whereby the absorption and scattering events responsible for the attenuation of the traversing light may be identified and quantitated more clearly. This invention has particular application for the early detection of breast cancer, a screening procedure most frequently performed by x-ray means (mammography), light transmission (diaphanography), thermal imaging (thermography), and ultrasound.

2. Description of the Related Art

The non-invasive examination of the interior of materials has been a familiar procedure for many years. This is particularly true for the radiological examination of human tissues using x-ray sources. Many such x-ray techniques have been improved significantly in recent years, both as regards safety and resolution. Safety has been increased by means of greatly improved films, permitting dramatic reductions of radiative doses and the risks associated with exposure to x-rays. Applied to the detection of breast cancer, x-ray examination (mammography) is considered the standard and most successful procedure for detecting early signs of disease, despite a false negative rate often exceeding 20%. False positive results often equal or exceed true positive results.

Another method for detecting breast cancer uses transmission spectroscopy where a bright, quasi-monochromatic light emitter is placed in proximity to the breast surface, and a television recording or digital image is made of tissue illuminated by the light transmitted through it. A similar scan is made at a slightly different wavelength, and the two images are combined by means of an enhancement algorithm. The final image is then examined by a trained interpreter who makes estimates as to probable carcinoma or disease based on various absorption criteria. Such instruments are of the type sold under the tradename "Spectrascan Model 10" manufactured by Spectrascan, Inc. Once again, for this procedure the false negative rate often exceeds 25%, even with a trained interpreter, and false positive rates may be very high.

Mammography, spectral transmission, and ultrasound are often used in conjunction with one another as a means of detecting carcinomas and other lesions by one method when not detected by another. Ultrasound techniques are used primarily to detect nodules or smaller non-palpable masses. It is in the hope of detecting the onset of carcinomas before they are detected by ultrasound that mammography and spectral transmissions have held their greatest promise, yet their most successful applications also have been for the detection of small, non-palpable masses. The combination of methods still produces an unacceptably high level of false negative (and positive) results.

The relatively high levels of false positives referred to above and associated with all of the methods are perhaps even more distressing than the high incidence of false negative results. If all examinations by a certain technique were classified as positive (on the basis of a given screening technique), then the technique would be considered by its proponents as perfect, since all lesions would have been detected. But a huge number of needless biopsies would have been performed, and if every examination required a biopsy, then the screening technique itself would be useless. Girolamo and Gaythorpe, in their recent CRC Critical Review (1984) of Clinical Diaphanography and related measurements (mammography, ultrasound, thermography, etc., present data of many practitioners that show that the number of biopsies performed often exceeds ten times the number of true breast carcinomas found. The diagnostic procedures seem to have some utility, but hardly seem reliable. Indeed, both mammography and diaphanography, currently the most reliable procedures, seem incapable of detecting deep lesions smaller than about 2 mm in diameter.

Since the interpretation of both mammographs and diaphanographs requires trained interpreters, and such training in itself requires a phenomenological correlation between things "seen" and carcinomas discovered by biopsy or other surgical procedure, one should ask the question: Is the information disclosed consistent with the measurement made?

In the case of x-rays (mammography), the uncomfortable and often painful examination procedure requires, for its most useful application, that the examined breast be compressed to make it more uniformly thick to yield "even penetration by the x-rays, less difference in radiographic density of the chest wall area and the nipple, and reduced radiation dose . . . " (Girolamo and Gaythorpe, loc. cit.). Yet, as has already been mentioned, the ability of such measurements to identify early true carcinomas remains very low. Light transmission measurements seem to yield even worse results. Mammograms disclose differences in the absorption of x-rays by various tissue constituents, yet there are many sources for transmission differences that are unrelated to carcinoma of the breast. It is only by training and experience that mammograms may be interpreted properly. But if we seek to detect an abberant cellular morphology of some cells whose extent is often only tens of micrometers, are x-rays whose wavelength are a few nanometers the most suitable radiation source? The mismatch in the wavelength of x-rays with the size of cancerous cells would suggest not. However, the ability of x-rays to penetrate through otherwise opaque material suggests some vague utility for detecting cumulative abberant absorptions of layers upon layers of diseased cells. A nodule of two millimeters diameter detected by x-ray means and confirmed by subsequent biopsy is surely a well-developed carcinoma rather than an early manifestation of cancer. By the time x-ray techniques detect such lesions, the corresponding carcinoma is probably a later manifestation of disease. True, such detection is often earlier than detection by palpation alone and can improve survival statistics, but it surely cannot be called "early detection" which must occur at the cellular level, i.e. at the first occurrence of a cancerous cell. This "early detection" misnomer persists among proponents of mammography.

Light transmission or diaphanographic methods have similar problems. Although light wavelengths in the near infrared provide a better match to the size of mammalian cells, or at least the regions within cells where the cancerous state is confirmed by cytological examination, the tremendous scattering and attenuation of light by tissue makes it difficult, at best, to develop consistent deductions of probable lesions, especially deep in the tissue. Because of the multiple scattering of light within tissue, the detected signals are degraded and accordingly must carry very little information with them about the environment deep within the tissue. The most "spectacular" observations achieved by light transmissions and its variants have been the graphical disclosures of near surface phenomena and features such as veins, implants, cysts, nipple regions, etc.

In reviewing the literature describing x-ray and light measuring techniques for the early detection of breast cancer, I have become aware of a new approach and instrumentation by which light may be used to yield more significant information about the sources of its scattering during its traversal of the breast. Although my discussion has centered primarily upon applications relating to the detection of breast cancer, it will be obvious to those skilled in the art that the method and apparatus may be applied equally well to other tissue, as well as semi-opaque objects not so-related.

BRIEF SUMMARY OF THE INVENTION

My invention is comprised of eight basic interacting elements: (1) a monochromatic, highly collimated, polarized or unpolarized light source which preferably will be a continuous or pulsed laser operating in the red or near infrared spectrum; (2) an optical transmission means, such as a fused and highly polished, flaired, optical fiber bundle by which the light so-generated is brought to the surface of the semi-opaque object to be examined; (3) a coupling fluid that eliminates any air interface between the transmission means and the object being illuminated; (4) an optical collection means located at a different position on the object and equivalently coupled by fluid means to the object transmitting the light incident thereon; (5) transmission means by which light collected by said collection means is transmitted to (6) a very high gain light amplification means that preserves the spatial distribution of intensity levels incident before amplification; (7) a high resolution detection means comprised of a two-dimensional array of detector pixels that again preserve the spatial distribution of the amplified light intensities incident thereon, and providing signals to (8) storage, display, and computer means.

In this manner, the light coupled into the object to be examined is well-defined in terms of its wavelength, polarization, and incident direction. Reflections at the object surface are minimized by inserting an index matching fluid between the light transmission means and the object. Transmitted light is then removed at a specific angle/position on the object with respect to the direction/position of the incident light, with a similar index matching fluid between the object and collector means. It is important to note that the direction of the collected transmitted light is not generally along the line of the incident radiation. A high resolution detector follows an image intensifier to yield a detailed image of the emerging light at the object surface.

DESCRIPTION OF THE PREFERRED EMBODIMENTS

Unlike conventional diaphanographic techniques whereby light is transmitted through the semi-opaque object and, upon emergence therefrom, is photographed or otherwise recorded by means solely of the transmitted light, the image of the present invention is created by transferring light at the surface directly to detection and recording means before such light may be diffused or defocussed by said surface. In addition, the method of the present invention emphasizes the detection of light *scattered* within the object into a *specific* angular direction with respect to the direction of the incident illumination. Another important objective of the invention is to make use of a measure of the coherence of the scattered light after scattering so that the degree of internal degradation may be quantified and correlated with the angle of scattering and the distance through the intervening material it has traveled from time of injection to time of detection.

An important element of the invention is the incorporation of light amplification means into the detection means to permit use of modestly low incident laser power levels as well as to compensate for the huge losses that may well occur within the object itself. Such light amplification means may be controlled so that the overall gain of the system may compensate for differences in optical path lengths of the examined structures.

It will be appreciated by those skilled in the art of light transmission measurements that this invention provides far greater detail of the transmission and scattering processes occurring within the object than has been attainable hitherto. Accordingly, my invention will find great utility in the interpretation and explanation of the structural elements of the semi-opaque object itself, but, like other methods, will require a new set of phenomenological correlations of the new information disclosed with the results of invasive examination.

I now shall explain in detail how the interaction of the eight elements alluded to briefly in the invention summary yield an instrument of exceptional sensitivity for the examination of the interior of semi-opaque objects. Since the most important application of this instrument will be in the area of cancer detection within a human breast, the preferred embodiments of the invention will be illustrated by frequent reference thereto.

Figure 1:
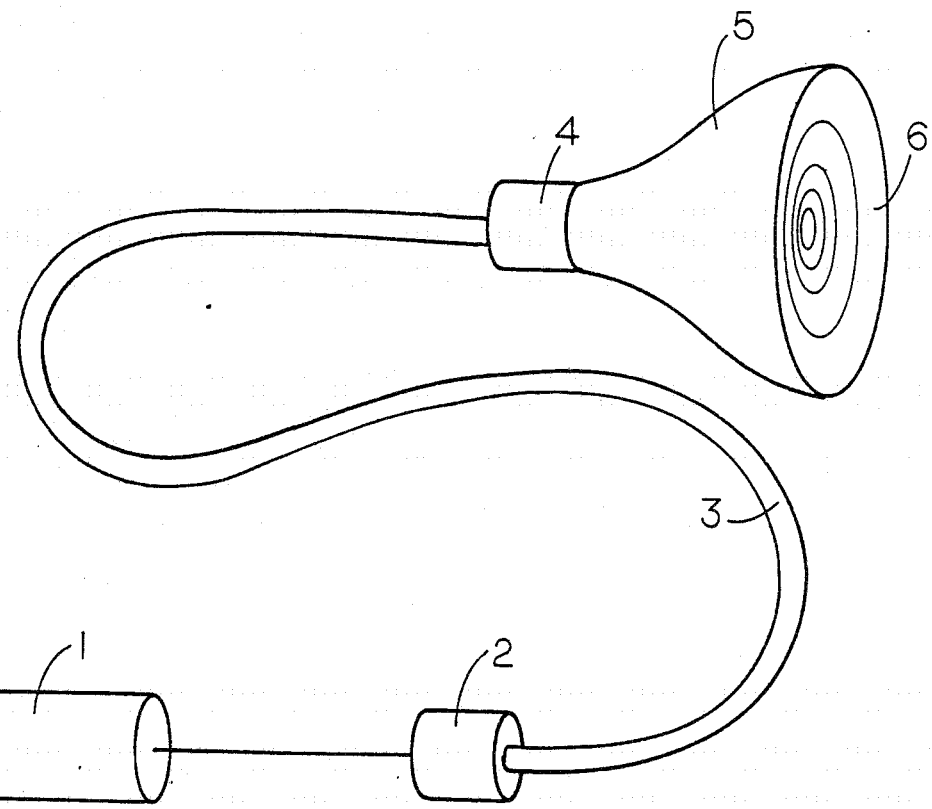
FIG. 1 shows the preferred embodiment of the incident light source coupled by optical fiber means into a flaired and fused, concave optical bundle.

FIG. 1 presents a view of the key elements of the illumination system. A laser 1 or similar light source produces a plane polarized, circularly polarized, or unpolarized monochromatic, highly collimated light beam which impinges upon a lens element 2 coupled to a long flexible optical fiber means 3. The laser should produce monochromatic light of red or near infrared wavelengths between, say, 600 and 4000 nm, and produce on the average a beam power of the order of 10 to 100 mW. The laser may be operated continuously, or pulsed, or even have its beam chopped. Pulsed or chopped operation can simplify some dark offset measurements and signal processing procedures performed later, though such beam interruptions are by no means essential. A He-Ne laser operating at 632.8 nm of the type manufactured by Melles-Griot or Jodan Laser would be reasonable choices in the red, whereas a He-Ne laser operating in the infrared at 1150 nm or 3390 nm of the type manufactured also by Jodan Laser would suffice for the infrared. The actual choice of the most suitable infrared wavelength will depend on the properties of the object being examined. Human tissue has a high water content and, therefore sources emitting at the characteristic absorption bands of water should be avoided. The lens element 2 focuses the beam (of nominal 1 mm diameter) onto an optical fiber element 3 that may preserve the polarization of the beam or destroy all memory of polarization. The lens may be of conventional structure or a half pitch gradient refractive index (GRIN) lens of the type produced by Nippon Sheet Glass Co., Ltd. under the tradename "SELFOC." The optical fiber is terminated at the focal point of another lens or GRIN lens 4 to produce a nearly parallel output beam. This, in turn, may be coupled optionally into a flaired optical bundle 5 of the type manufactured by Bausch & Lomb with a flat or slightly convex surface 6 that is brought in contact with the semi-opaque object to be examined. The terminal fiber elements of the flaired optical bundle 5 alternatively may be fused to a fine array of GRIN lenses of the type commonly used in compact "Xerographic" machines. Such terminations insure that the emerging light detected will be restricted to those remaining parallel to a given direction with minimal dispersion before entering the semi-opaque object. The entire transmitter section should be covered and light tight except for the small portion of optical bundle or GRIN lens to be placed in contact with the object at a specific entrance location thereon. In this manner, all stray light contributions should be removed. Alternatively, a laser head itself may be held directly against the object with some refractive index matching fluid between the output laser mirror and the object. For safety reasons, however, some type of indirect fiber coupling may still be preferable since the laser head will be operated at a high voltage.

Figure 2:
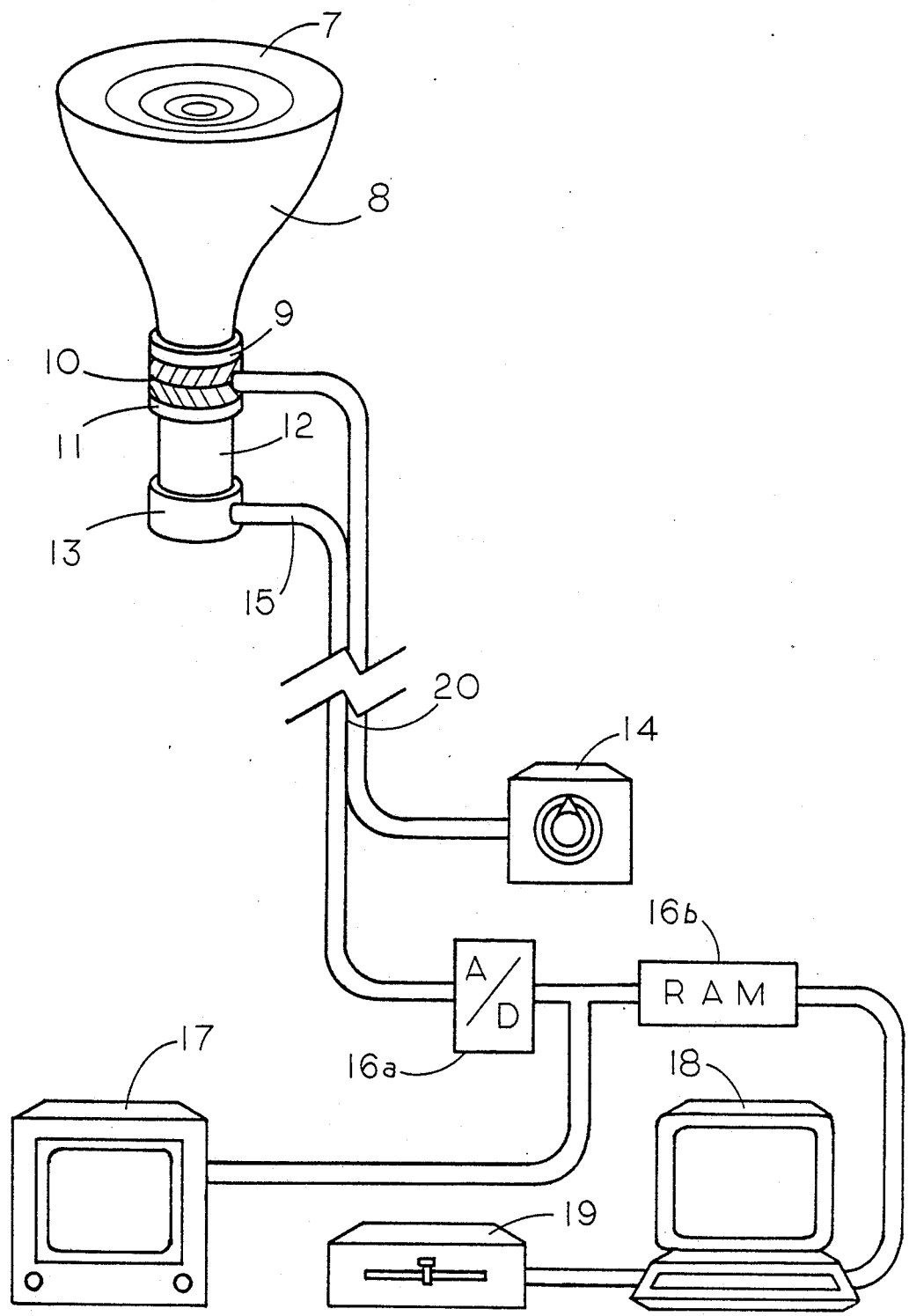
FIG. 2 presents a similar detailed view of the flaired optical bundle light collection means fused to the faceplate of an image intensifier whose output signal is coupled into a self-scanned CCD array which, in turn supplies signals to a video display and a computer means.

FIG. 2 presents the key elements of the transmitted light collection system. A flaired optical fiber bundle 8 with a similarly fabricated flat or concave surface 7 is joined to the optical faceplate photocathode 9 of a microchannel plate light amplifier or image intensifier 10 of the type manufactured by Litton Electron Tube Division containing a red sensitive S-20, or equivalent, photocathode 9 and a P46, or equivalent, phosphor fiber plate 11. Such image intensifiers, including their various formats of C-plates, chevron plates, or Z-plates are capable of producing photon amplifications of $10^6$ or greater. An optical fiber endplate 12 is then joined to a very high resolution, two-dimensional charge coupled device (CCD) array 13 of the type manufactured by Photometrics, having as many as 2048×2048 pixels. All elements are joined in optical contact using refractive index matching materials such as fluids or transparent gels of the types manufactured by R. P. Cargill Laboratories, Inc.

The microchannel plate image intensifier 10 is powered by a variable gain power supply 14. The CCD output is sent over cable 15 to an analog-to-digital converter 16A and then stored in a computer memory means 16B accessible for display on a high resolution monitor 17 or for digital image enhancement processing by a computer 18 and/or storage in rotary memory means 19.

Instead of a CCD array, which transmits the values of its pixel elements sequentially, image collection may be accomplished using a two-dimensional array of photodiodes whose output signals are sampled in parallel and held or frozen periodically while they are converted. These analog values would be multiplexed and then converted sequentially to digital representations for storage in the computer memory means or recording on rotary memory means 19.

Figure 3:
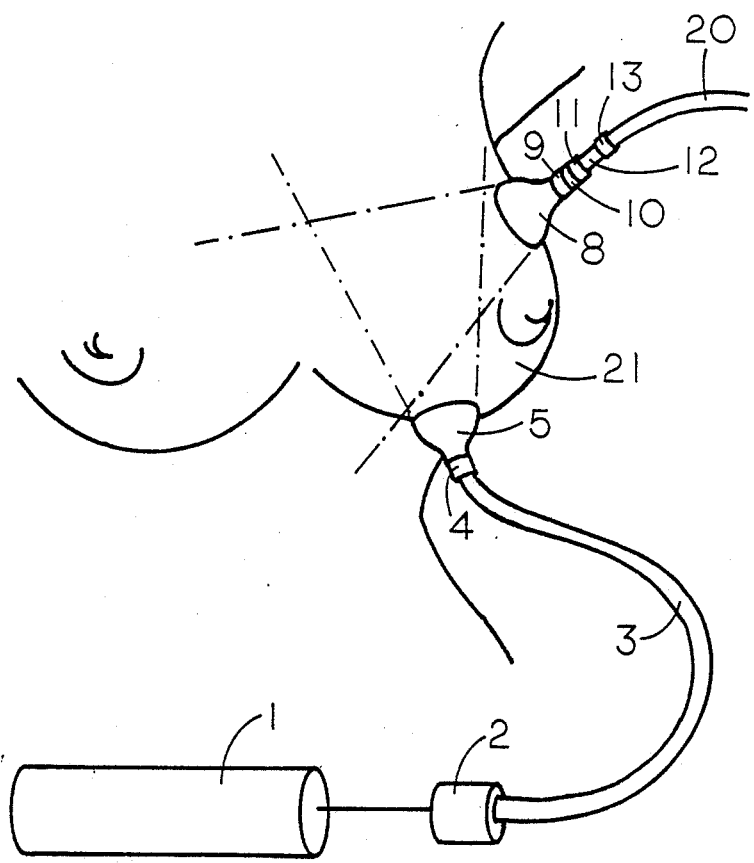
FIG. 3 shows a typical placement during breast examination.

FIG. 3 shows the transmitter and collector structures in a particular orientation with respect to a female breast 21. A single cord 20 contains the CCD output cable 15 and the microchannel power cord. Note that the two flaired optical fiber faceplates 5 and 8 are each in contact with specific entrance and exit surfaces of the breast. An important feature of this invention is the contact required between the surfaces of the transmitter or collector with the object being examined. This is shown more clearly in FIG. 4 where an index matching means 22 similar to the types made by R. P. Cargill Laboratories is placed between the object 21 and the optical element 5. It is important to emphasize that for maximum data retrieval of scattered and transmitted light, the transition from one material to the next must be coupled efficiently so that interface scattering, reflections and other losses be kept to an absolute minimum. An index matching fluid of refractive index 1.4 to 1.5 should suffice for the case human skin or similar proteinaceous material.

Figure 5:
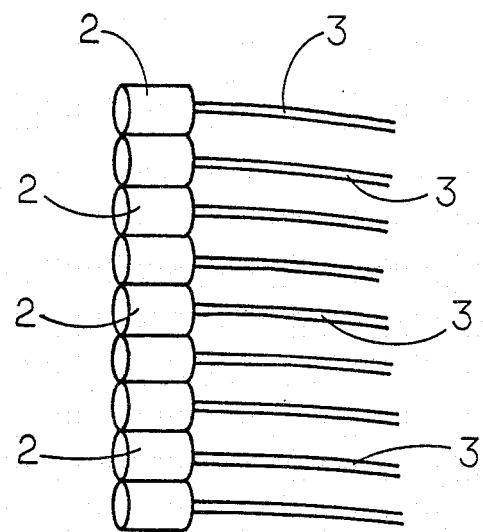
FIG. 5 shows a fine array of gradient refractive index lenses, each attached to discrete fibers.

FIG. 5 shows the coupling of a set of optical fibers into an array of gradient refractive index lenses. These arrays are of the type frequently found in "Xerox-type" copy machines. This type of coupling permits, for half pitch GRIN elements, a highly restricted acceptance angle and field of view when light scattered from the object enters the GRIN lens which, in turn, focuses it into the optical fiber attached thereto. Conversely, if the light is transmitted from a fiber into a GRIN lens, it emerges nearly parallel. Attachment of GRIN arrays to the various optical fiber elements of the coupling structures 5 or 8, will be useful in certain configurations when highly collimated light is required or it is necessary to restrict the detected field of view.

The coupling structures 5 and 8 of FIGS. 1 and 2, respectively, need not be of large extent. In the preferred embodiment of the invention in FIG. 1, the GRIN lens 4 will have typically an output diameter of about 2 mm. The optical fiber coupler 5 may have a magnification of the order of 10×, i.e. the emitting surface 6 will have a diameter of the order of 20 mm or even less.

An annoying characteristic of laser beams is their non-uniform intensity profile. If they emit in the so-called TEM$_{oo}$ mode, the profile is Gaussian. Such a non-uniform profile is of the form $$I(r) = I_o \exp[-2(r/r_o)^2], \quad (1)$$

where I (r) is the intensity at a distance r from the beam axis, $I_0$ is the axial intensity at r=0, and $r_0$ is the distance from axis at which the intensity has fallen to $1/e^2$ its axial value. It is well known that the spatial regularity of a laser may be randomized upon passing the beam through a multimode optical fiber. I have found that the structure 2-3-4 of FIG. 1 results, for the case of multimode fiber 3, in an emerging beam at 4 that is nearly parallel, unpolarized, and uniform over a diameter approximately equal to the diameter of the GRIN lens 4. This is independent of the polarization state of the incident collimated illumination. If a completely homogeneous and parallel incident beam is required to pass through the object, then this 2-3-4 combination would be the preferred structure of the light transmitting module of FIG. 1. The flaired optical fiber coupler 5 would be removed, and the GRIN lens 4 would be coupled directly into the object 21 by means of an index matching fluid layer 22 between the object 21 and the lens 4. For many applications, however, the GRIN lens 4 would be coupled into the flaired optical bundle 5 whose subsequent coupling into the object would insure still a strong forward directed beam through the object.

Prior to image enhancement processing by the computer 18 of the digital image generated from the CCD array 13 of the transmitted light from the object coupled into the collector structure 8, it may be required to know the relative positions of the transmitter (FIG. 1), and collector (FIG. 2) structures relative to one another. Not only should their spatial coordinates be described, but so also should the angle of scattering between the transmitter axis 23 and the collecter axis 24 shown in FIG. 6. It is important to have these measurements so that the path lengths through the object, the region of intersection 25, and the angle of scattering 26 may be calculated therefrom. There are many means by which such coordinates and axial directions be known as will be appreciated by those skilled in the art. For example, the transmitter and collector structures may be attached to position and angle encoding means frequently employed in robotics such as the chemical robot systems of Zymark, among many others.

Figure 6:
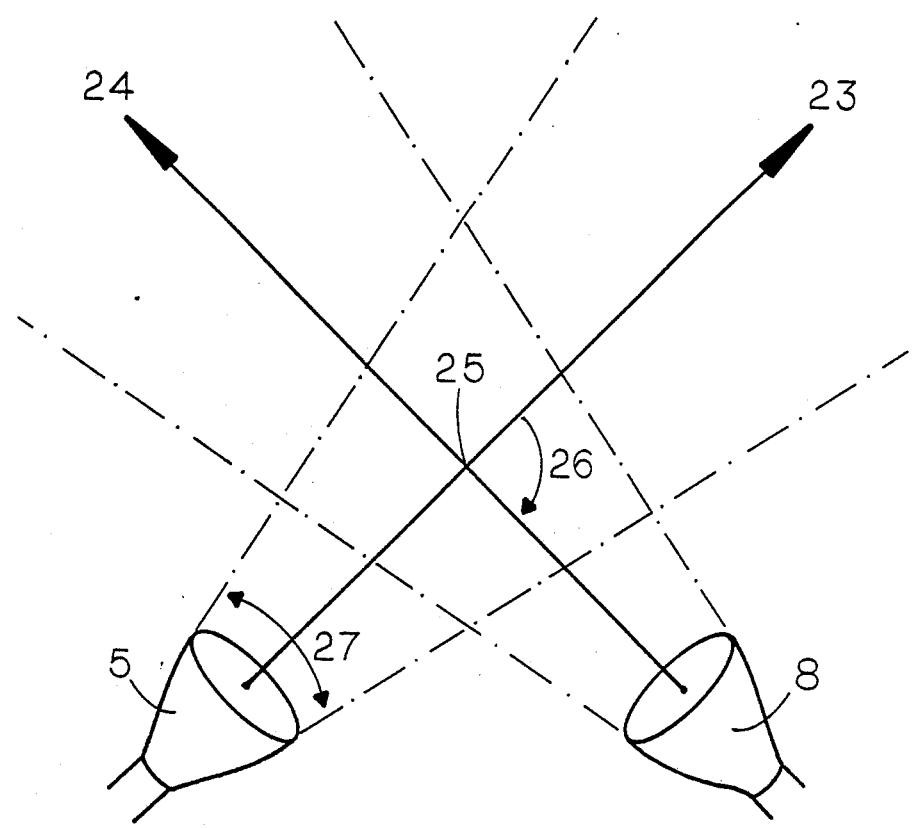
FIG. 6 shows the optical axis of transmitter and collector means, their region of intersection, and relative motions therebetween.

As will be apparent from FIG. 6, both transmitter 5 and collector 8 means may each be moved independently of one another. This important feature of the invention implies that the interior of the object may be scanned in different manners. For example, by holding the collector 8 fixed and rotating the transmitter 5 along the directions indicated by 27, the features of the object along the detector axis 24 may be illuminated sequentially. Conversely, fixing the transmitter 5 and rotating the collector 8 so that the region of intersection 25 remain the same would result only in the variation of angle 26 angle indicated. Thus the scattering properties of the region of intersection 25 as a function of scattering angle may be observed. Once the data were image enhanced, it might well be possible to identify, or at least characterize, the small inhomogeneities or particles located in this region 25 on the basis of methods developed earlier by the inventor and Quist.

As will be apparent to those skilled in the art of servo mechanisms, the transmitter 5 may be controlled by mechanical means, preprogrammed to remain in contact with the object, to scan the entire volume of the object or any selected subvolume thereof. With the cooperative motion of the collector 8, every element of the object may be subjected to multi-angle examination. The light transmitted through the object will undergo, in general, huge degradations as it passes through semi-opaque regions such as found in the human breast. Much of this degradation is the result of multiple scattering which prevents the collector section from receiving but small quantities of directly scattered light. It remains for image enhancement techniques to process the collected, high resolution data and enhance features degraded by such multiple scattering processes. Because the transmitter and collector are not constrained to a single aspect with respect to one another, the enhancement process will be even more successful in resolving those features responsible for the major internal scattering events. Further measurement of coherence effects manifest by the quantity and size of "speckle" remaining in the collected light may be quantitated for the subsequent estimation of the degree of multiple scattering that occurred during the traversal of the object. Digital image enhancement techniques, often referred to as signal recovery, have reached high levels of development. The enhancement of pictures from deep space produced by the Voyager spacecraft is a typical example. A wealth of references and methodologies are presented in the January 1987 issue of the Journal of the Optical Society of America A, Vol. 4, Number 1, dedicated to Signal Recovery techniques.

The present invention achieves its measurements in sharp contrast to prior art. This is most easily seen in the consideration of the preferred embodiments for the examination of human breast tissue. Mammographic and diaphanographic methods illuminate the entire breast or a reasonably large fraction of it. The present invention concentrates on fine beam illumination of a small region within the breast and a collimated detection thereof. Prior art generally measures radiation (x-ray or light) passing straight through the breast. The present invention emphasizes the ability to examine the scattered and transmitted radiation at many angles of observation with respect to a defined volume within the breast. In addition, in contrast to diaphanography, the present invention emphasizes the need to eliminate surface interface effects. As is well known, radiation striking an interface between two surfaces of refractive index $n_1$ and $n_2$, respectively, will reflect back from that surface. The fraction of radiation reflected thereby relative to the light radiation incident thereon is given, for normal incidence, by $$R = (n_1 - n_2)^2 / (n_1 + n_2)^2 \qquad (2)$$

For the case of human tissue having a dehydrated value of about $n_1 = 1.5$, the reflection at the skin-air interface will be about 4% where $n_2 = 1.0$, for air. For non-normal incidence, this reflected fraction increases to 100% at the critical angle $$\theta_c = \sin^{-1}(n_2/n_1). \qquad (3)$$

Figure 4:
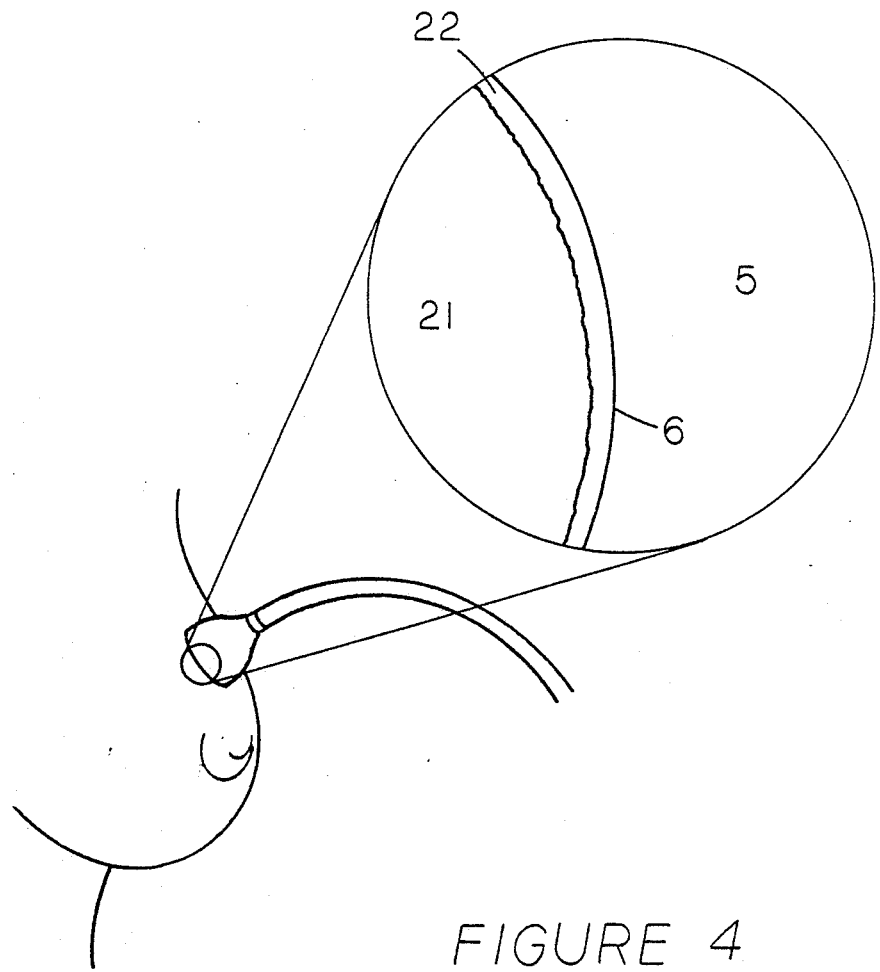
FIG. 4 shows the interface between the object and the transmitter or collector flaired optical fiber bundle with an index matching fluid therebetween.

For $n_1 = 1.5$ and $n_2 = 1$, $\theta_c = 41.8°$. This means that any light internal to the breast, in this example, and incident at an angle greater than about 42° with respect to the normal will be completely reflected. Multiple scattering within such semi-opaque objects insures that a great fraction (over 50%) of all light transmitted through, for example, breast tissue will be reflected back into the breast to be further degraded and absorbed. The present invention pays particular attention to the need of preventing such surface-induced degradations by coupling the light incident on the air-object interface from within the object to the collector means using refractive index matching fluids 22 as indicated in FIG. 4.

Figure 7:
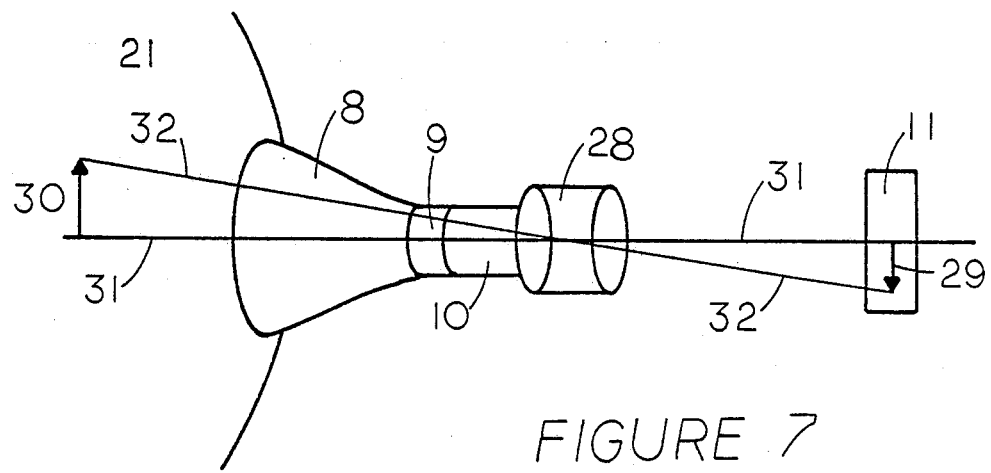
FIG. 7 shows the collector means with an added lens structure producing an intensified image at the detection means of scattering elements within the object.

In the absence of multiple scattering, the measurement shown in FIG. 6 corresponds to the familiar Fraunhofer scattering configuration. The small particles in region 25 scatter light which is then collected at a great distance from the particles relative to their size. If we wanted to image the objects themselves rather than their Fraunhofer diffraction/scattering patterns, then an imaging lens structure 28 as shown in FIG. 7 would be required. This lens structure would form an image 29 of the elements 30, say, within the object 21 at the detector array 11 after collection at 8 and intensity amplification at 9. The optical fiber coupling 10 shown between the image intensifier plate 9 and array 11 of FIG. 2 would now include intermediate lens structure 28. Standard optical tracing rays are indicated by 31 and 32, respectively. The lens structure 28 or other lens elements may also be placed in front of collector means 8 or between other indicated elements of the collector structure so that the resulting image would be optimized for the wavelength and object elements examined. Care to couple all such lens elements as discussed hereinbefore must be exercised at all times.

As will be apparent from the information hereinbefore disclosed, there are many modifications and variations of the preferred embodiments discussed that will serve the purpose of my invention equally well. All such modifications and variations are included herein, and form obvious extensions thereof.

I claim:

1. A method for the examination of the interior of a semi-opaque object by collimated light means comprised of the following steps:
    A. forming a narrow, collimated beam of light;
    B. passing such beam into an optical transmission means;
    C. coupling said optical transmission means onto said semi-opaque object at a specified entrance surface region using a refractive index matching means, suitably selected to minimize the refractive index discontinuity between that of said optical transmission means and that of said semi-opaque object;
    D. coupling that fraction of said light which has scattered within and impinged upon a specified surface exit region of said object, by similar refractive index matching means to an optical collection means at said specified surface region;
    E. coupling said optical collection means into a light amplification means which preserves the spatial intensity variations incident thereon and collected at said specified surface region by said optical collection means;
    F. impinging said amplified light on an array of photodetectors;
    G. converting each detected intensity corresponding to each photodetector element of said array into a numerical value and then transmitting each such value into a memory storage means;
    H. processing and analyzing said numerical values in said memory means by computer means; and characterizing thereby the region of said examined object causing the spatial variation of said intensity values;
    I. repeating said measurement at different orientations of said incident coupled optical transmission means and said coupled optical collection means with respect to said specified surface regions;
    J. varying said entrance and exit surface regions and repeating steps G, H and I;
    K. characterizing thereby the inhomogeneities within said semi-opaque object causing the spatial variations of the said detected intensity values.

2. The method of claim 1 where said collimated beam of light is essentially monochromatic.

3. The method of claim 1 wherein the narrow, collimated beam of light is from a laser.

4. The method of claim 3 where the laser light is linearly polarized.

5. The method of claim 3 where the laser light is unpolarized.

6. The method of claim 3 where said optical transmission means includes a first lens element focusing said laser beam onto a multimode optical fiber, and other end of said fiber is terminated at the focal point of a second lens element.

7. The method of claim 1 where the light amplification means is a microchannel plate.

8. The method of claim 7 where the microchannel plate is a chevron plate.

9. The method of claim 7 where the microchannel plate is a C-plate.

10. The method of claim 7 where the microchannel plate is a Z-plate.

11. The method of claim 1 where the array of photodetectors is comprised of photodiodes.

12. The method of claim 1 where the array of photodetectors forms a charge coupled device.

13. The method of claim 3 where the laser is a He-Ne laser.

14. The method of claim 3 where the laser produces red light.

15. The method of claim 3 where the laser produces infrared light.

16. The method of claim 1 where the semi-opaque object is a human breast.

17. The method of claim 1 where the conversion of said detected intensities is achieved by an analog-to-digital converter.

18. The method of claim 1 wherein said amplified light is made to impinge upon a lens element before impinging on said array of photodetectors forming, thereby, an image of a region interior to said object on said photodetector array.

19. The method of claim 1 where the processing of said numerical values in said memory includes the processes of signal recovery.

20. The method of claim 6 where each said lens element is a half pitch gradient refractive index lens.

21. The method of claim 1 where said refractive index matching means is a fluid.

22. An instrument for the examination of the interior of a semi-opaque object by collimated light means comprised of:
    A. Collimated light means producing a narrow beam of light;
    B. Collimated light beam optical transmission means
    C. Coupled onto said semi-opaque object by refractive index matching means suitably selected to minimize the refractive index discontinuity between that of said optical transmission means and that of said semi-opaque object at a specified entrance surface;
    D. Optical collection means; said optical collection means being coupled by similar refractive index matching means to a specified exit surface region of said object through which light scattered within said object has scattered thereto;

E. Light amplification means whereby light collected from said object in step D is amplified in intensity while maintaining its spatial variations at said optical collection means;

F. Optical lens means by which said amplified light spatial variation is imaged on G. Photodetector array means transmitting output signals proportional to incident intensities to H. Analog-to-digital conversion means whereby each signal at each photo-detector element in converted into a digital representation stored in I. Memory means of a J. Computer processing means.

23. The instrument of claim 22 where said collimated beam of light is essentially monochromatic.

24. The instrument of claim 22 wherein the narrow, collimated beam of light is from a laser.

25. The instrument of claim 24 where the laser light is linearly polarized.

26. The instrument of claim 24 where the laser light is unpolarized.

27. The instrument of claim 24 where said optical transmission means includes a first lens means focusing said laser beam onto a multimode optical fiber, and other end of said fiber is terminated at the focal point of a second lens means.

28. The instrument of claim 22 where the light amplification means is a microchannel plate.

29. The instrument of claim 28 where the microchannel plate is a chevron plate.

30. The instrument of claim 28 where the microchannel plate is a C-plate.

31. The instrument of claim 28 where the microchannel plate is a Z-plate.

32. The instrument of claim 22 where the array of photodetectors is comprised of photodiodes.

33. The instrument of claim 22 where the array of photodetectors forms a charge coupled device.

34. The instrument of claim 24 where the laser is a He-Ne laser.

35. The instrument of claim 24 where the laser produces red light.

36. The instrument of claim 24 where the laser produces infrared light.

37. The instrument of claim 22 where the semi-opaque object is a human breast.

38. The instrument of claim 22 where the conversion of said detected intensities is achieved by an analog-to-digital converter.

39. The instrument of claim 22 where said amplified light is made to impinge upon a lens element before impinging on said array of photodetectors forming, thereby, an image of a region interior to said object on said photodetector array.

40. The instrument of claim 22 where said computer processing means includes the processes of signal recovery.

41. The instrument of claim 27 where each said lens means is a half pitch gradient refractive index lens.

42. The instrument of claim 22 where said refractive index matching means is a fluid.

43. The method of claim 1 where measurement is made of the relative orientations and positions of the transmission and collection means coupled to the semi-opaque object being examined.

44. The method of claim 43 where said measured relative orientations and positions of said optical transmission and collection means coupled to said semi-opaque object being examined are recorded.

45. The method of claim 44 where the measurements derived therein are used to calculate the path through the semi-opaque object.

46. The method of claim 44 where the measurements derived therein are used to calculate the locations of the scattering objects therewithin and the angle of scattering therefrom with respect to the direction of the incident light.

47. The method of claim 3 where said processing and analysing of said collected numerical values include determination of the degree of coherence in said collected values.

* * * * *